United States Patent
Weinschenk, III et al.

(10) Patent No.: US 6,645,246 B1
(45) Date of Patent: Nov. 11, 2003

(54) INTRAOCULAR LENS WITH SURROUNDED LENS ZONE

(75) Inventors: Joseph I. Weinschenk, III, Ft. Worth, TX (US); Charles X. Liao, Irvine, CA (US); Massoud Ghazizadeh, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 161 days.

(21) Appl. No.: 09/657,325

(22) Filed: Sep. 7, 2000

Related U.S. Application Data
(60) Provisional application No. 60/154,554, filed on Sep. 17, 1999.

(51) Int. Cl.[7] .................................................. A61F 2/16
(52) U.S. Cl. .................... 623/6.37; 623/6.13; 623/6.22; 623/6.27
(58) Field of Search ........................... 623/6.13, 6.22, 623/6.27, 6.37; A61F 2/16

(56) References Cited

U.S. PATENT DOCUMENTS

| | | | |
|---|---|---|---|
| 1,483,509 A | 2/1924 | Bugbee | |
| 2,129,305 A | 9/1938 | Feinbloom | |
| 2,274,142 A | 2/1942 | Houchin | |
| 2,405,989 A | 6/1946 | Beach | |
| 2,511,517 A | 6/1950 | Spiegel | |
| 3,031,927 A | 5/1962 | Wesley | |
| 3,034,403 A | 5/1962 | Neefe | |
| RE25,286 E | 11/1962 | Decarle | |
| 3,210,894 A | 10/1965 | Bentley et al. | |
| 3,227,507 A | 1/1966 | Feinbloom | |
| 3,339,997 A | 9/1967 | Wesley | |
| 3,420,006 A | 1/1969 | Barnett | |
| 3,431,327 A | 3/1969 | Tsuetaki | |
| 3,482,906 A | 12/1969 | Volk | |
| 3,542,461 A | 11/1970 | Girard et al. | |

(List continued on next page.)

FOREIGN PATENT DOCUMENTS

| | | | |
|---|---|---|---|
| AU | 3225789 | 10/1989 | |
| DE | 2702117 | 7/1978 | |
| DE | 3246306 | 6/1984 | |
| DE | 101 25 829 A1 | * 11/2002 | ............ A61F/2/16 |
| EP | 0246216 | 11/1987 | |
| EP | 0329981 | 8/1989 | |
| EP | 0337390 | 10/1989 | |
| EP | 0342895 | 11/1989 | |
| EP | 0351471 | 1/1990 | |
| EP | 0566170 | 10/1993 | |

(List continued on next page.)

OTHER PUBLICATIONS

Thornton, Accommodation in Pseudophakia, 25, pp. 159–162.

Video Tape "New Elliptical Acco. IOL for Cataract Surgery," shown at ASCRS Symposium on Apr. 10, 1999 (Video Enclosed).

(List continued on next page.)

*Primary Examiner*—David H. Willse
*Assistant Examiner*—Javier G. Blanco
(74) *Attorney, Agent, or Firm*—Peter J. Gluck

(57) ABSTRACT

An intraocular lens for use in a mammalian eye includes an optic adapted to focus light toward a retina of the mammalian eye and, in cooperation with the mammalian eye, to provide accommodation, the optic including a first portion adapted to move in response to the action of the mammalian eye; and a second portion surrounded by the first portion, and having a higher index of refraction than the first portion and/or being less deformable than the first portion in response to forces exerted by the mammalian eye.

37 Claims, 2 Drawing Sheets

U.S. PATENT DOCUMENTS

| | | |
|---|---|---|
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Guilino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsuetaki et al. |
| RE32,525 E | 10/1987 | Pannu |
| 4,702,244 A | 10/1987 | Mazzocco |
| 4,704,016 A | 11/1987 | de Carle |
| 4,720,286 A | 1/1988 | Bailey et al. |
| 4,725,278 A | 2/1988 | Shearing |
| 4,731,078 A * | 3/1988 | Stoy et al. ..................... 623/6 |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,888,012 A | 12/1989 | Horn et al. |
| 4,888,015 A | 12/1989 | Domino |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Milge et al. |
| 4,976,732 A | 12/1990 | Vorosmarthy |
| 4,990,159 A | 2/1991 | Kraff |
| 4,994,082 A | 2/1991 | Richards et al. |
| 4,994,083 A * | 2/1991 | Sulc et al. ..................... 623/6 |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,152,788 A * | 10/1992 | Isaacson et al. ............... 623/6 |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,549,760 A | 8/1996 | Becker |
| 5,562,731 A | 10/1996 | Cumming |
| 5,578,081 A | 11/1996 | McDonald |
| 5,607,472 A | 3/1997 | Thompson |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,776,192 A * | 7/1998 | McDonald ..................... 623/6 |
| 5,800,533 A * | 9/1998 | Eggleston et al. ............. 623/6 |
| 5,814,103 A | 9/1998 | Lipshitz et al. |
| 5,843,188 A | 12/1998 | McDonald |
| 5,876,442 A | 3/1999 | Lipshitz et al. |
| 5,984,962 A * | 11/1999 | Anello et al. .................. 623/6 |
| 6,013,101 A | 1/2000 | Israel |
| 6,096,078 A | 8/2000 | McDonald |
| 6,117,171 A * | 9/2000 | Skottun ..................... 623/6.37 |
| 6,176,878 B1 * | 1/2001 | Gwon et al. ............. 623/6.37 |
| 6,217,612 B1 | 4/2001 | Woods |

FOREIGN PATENT DOCUMENTS

| | | |
|---|---|---|
| EP | 0691109 | 1/1996 |
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |
| GB | 2215076 | 9/1989 |
| WO | 8603961 | 7/1986 |

| | | | | |
|---|---|---|---|---|
| WO | 8700299 | 1/1987 | | |
| WO | 8707496 | 12/1987 | | |
| WO | 8902251 | 3/1989 | | |
| WO | 8911672 | 11/1989 | | |
| WO | 0 420 549 A2 * | 3/1991 | ............. | A61F/2/14 |
| WO | 9416648 | 8/1994 | | |
| WO | 9503783 | 2/1995 | | |
| WO | 9615734 | 5/1996 | | |
| WO | 9625126 | 8/1996 | | |
| WO | 9743984 | 11/1997 | | |
| WO | 0134067 | 5/2001 | | |

OTHER PUBLICATIONS

Partial Program Re: ASCRS Symposium, Showing Video Tape Shown Between Apr. 10–14, 1999.

Menzo et al. J Cataract Refract. Surg 24, Aug. 1998.

Fechner et al. J Cataract Refract. Surg 24, Jan. 1998.

Amo Specs, Model AC–218, 1992.

Chiron Vision, Nuvita MA20, 1997.

* cited by examiner

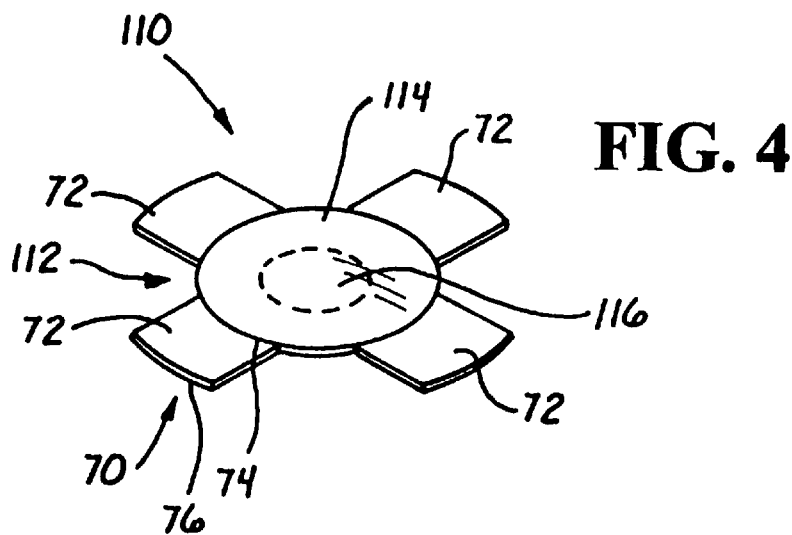
FIG. 4
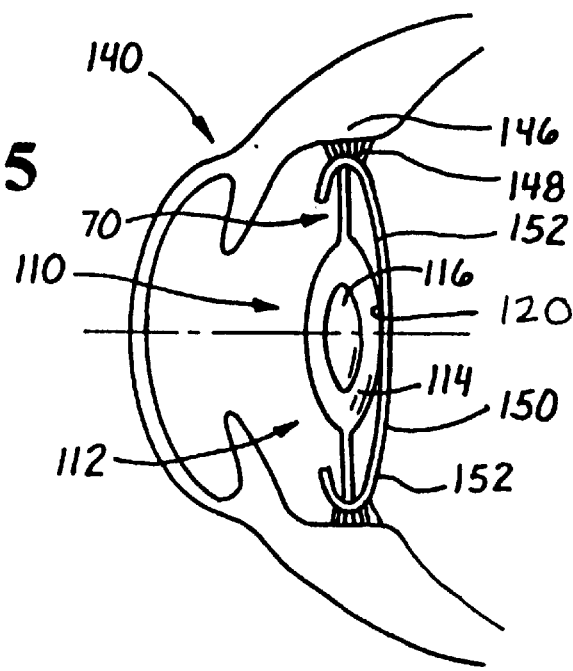
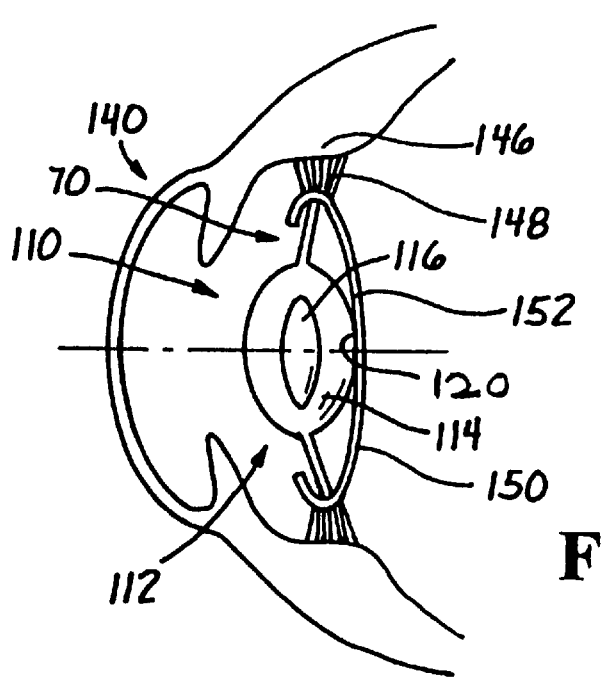
FIG. 5
FIG. 6

INTRAOCULAR LENS WITH SURROUNDED LENS ZONE

RELATED APPLICATION

This application claims the benefit of U.S. provisional application Ser. No. 60/154,554 filed Sep. 17, 1999, the disclosure of which is incorporated in its entirety herein by reference.

BACKGROUND OF THE INVENTION

The present invention relates to intraocular lenses (IOLs). More particularly, the invention relates to IOLs including surrounded lens zones which are adapted to provide accommodation in the eye.

The human eye includes an anterior chamber between the cornea and iris, a posterior chamber, defined by a capsular bag, containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near and distant vision, respectively. This ciliary muscle action shapes the natural crystalline lens to the appropriate optical configuration for focusing light rays entering the eye on the retina.

After the natural crystalline lens is removed, for example, because of cataract or other condition, a conventional, monofocal IOL can be placed in the posterior chamber. Such a conventional IOL has very limited, if any, accommodating ability. However, the wearer of such an IOL continues to require the ability to view both near and far (distant) objects. Corrective spectacles may be employed as a useful solution. Recently, multifocal IOLs without accommodating movement have been used to provide near/far vision correction.

Attempts have been made to provide IOLs with accommodating movement along the optical axis of the eye as an alternative to shape changing. Examples of such attempts are set forth in Levy U.S. Pat. No. 4,409,691 and several patents to Cumming, including U.S. Pat. Nos. 5,674,282 and 5,496,366. The disclosure of each of these patents is incorporated herein by reference. One problem that exists with such IOLs is that they often cannot move sufficiently to obtain the desired accommodation.

It would be advantageous to provide IOLs adapted for accommodating movement which can achieve an increased amount of accommodation.

SUMMARY OF THE INVENTION

New accommodating IOLs have been discovered. The present accommodating IOLs take advantage of employing an optic made of two different materials to enhance the accommodation achievable in the eye in response to normal accommodative stimuli. Thus, the present lenses provide for controlled vision correction or focusing for both near objects and far or distant objects. Further, a greater overall range of accommodation is often achieved. The present IOLs are relatively straightforward in construction and to manufacture or produce, can be implanted or inserted into the eye using systems and procedures which are well known in the art and function effectively with little or no additional treatments or medications being required.

In one broad aspect of the present invention, intraocular lenses (IOLs) are provided and comprise an optic adapted to focus light toward a retina of a mammalian eye and, in cooperation with the mammalian eye, to provide accommodation. The optic includes a first lens portion adapted to move in response to the action of the mammalian eye; and a second lens portion surrounded by the first lens portion of the optic, and having a higher refractive index or index of refraction than the first portion and/or being less deformable than the first portion in response to forces exerted by the mammalian eye.

The first lens portion is comprised of an optically clear material that is easily reshaped and/or is axially movable when exposed to force exerted by the mammalian eye. The second lens portion of the optic is comprised of an optically clear material having a higher refractive index than the first portion and/or being less deformable than the mammalian eye. For example, the first lens portion may have a refractive index of about 1.37 or less, while the second portion preferably has a refractive index of at least about 1.42. The difference in refractive index between the first and second portions may be in the range of at least about 0.03 and may be in the range of about 0.04 to about 0.1 or more. However, the second portion of the present optic may have a higher, lower or the same refractive index relative to the refractive index of the first portion. For example, both first and second portions of the present optics may have refractive indexes of about 1.37 or less. In one useful embodiment, both the first and second lens portions have refractive indexes of at least about 1.40 and/or at least about 1.42.

The second lens portion may be deformable or reshapable by the force exerted on the optic by the eye or may be substantially rigid in response to such force. As a result of this, potential materials for the second lens portion may vary significantly.

In one embodiment, the present lenses very effectively provide for both enhanced movement, for example reshaping and/or axial movement because of the substantially compliant or deformable first lens portion, while, at the same time, providing effective corrective optical powers with a reduced sized, e.g., thickness, lens because of the higher refractive index second lens portion. This combination of enhanced movement and high refractive index provides a substantial benefit in achieving accommodation in the mammalian eye.

Advantageously, the second lens portion of the optic is less deformable in the eye than is the first lens portion. Having a second portion with reduced deformability adds stability to the optic in the eye. The movement, for example, reshaping and/or axial movement, of the optic in the eye is achieved with reduced risk that such movement can misshape or otherwise distort the optic which can detrimentally affect the vision of the wearer of the IOL. In other words, the relatively rigid second lens portion of the optic may provide for a more controlled or reproducible movement of the optic in the eye relative to a similar optic without the second portion.

The second lens portion of the optic may be positioned at any suitable location in the optic. The second portion advantageously is substantially symmetrical about the optical axis of the optic. The second portion preferably is substantially centrally located within the first portion. The second lens portion is often secured to the first lens portion.

In one very useful embodiment, the first lens portion of the optic is adapted to be reshaped in response to the action of the mammalian eye. In particular, the first lens portion includes an anterior surface and is adapted to be reshaped in response to the action of the mammalian eye. This reshaping preferably is effective to change the curvature of the first portion, for example, the anterior surface of the first portion.

Such change in curvature alters the optical power of the optic and is effective in providing at least a portion of the desired accommodation. Alternately, and preferably in conjunction with the reshaping of the first lens portion, this first portion may be adapted to move axially in the mammalian eye in response to the action of the mammalian eye to provide additional accommodation.

Advantageously, the first and second lens portions of the optic are located so that their central axes are aligned with the optical axis of the optic. Looked at from another perspective, the second lens portion may be considered as a core or center of the optic while the first portion may be considered an outer layer or covering of the optic.

The reshaping or deformation of the first portion can cause an axial movement of the first portion which imparts an axial movement of the second portion of the optic. Axial movement of the portion of the optic with the greater dioptic power, most likely the high refractive index portion, e.g., the second lens portion, of the optic, has a relatively large effect on the accommodative power of the optic. Thus, axial movement of the second portion of the optic can be one feature of the present invention effective in providing accommodation. Of course, reshaping of the first portion in and of itself provides accommodative power, for example, by changing the curvature of the anterior surface of the first portion. The overall accommodative power of the optic in accordance with the present invention preferably is increased beyond the simple axial movement of a single lens of uniform composition, for example, because of the reshaping or deformation of the first lens portion.

In another very useful embodiment, a force transfer assembly is provided. This force transfer assembly has a first end coupled to the optic and a second end extending away from the optic and adapted to contact a posterior bag of the mammalian eye when the IOL is located in the mammalian eye. The force transfer assembly is adapted to transfer the force exerted by the eye to the optic to facilitate the movement of the optic. Preferably, the force transfer assembly is adapted to transfer the force exerted by the eye to the optic to facilitate at least one of reshaping the first portion in response to the action of the mammalian eye and moving the first portion axially in the mammalian eye in response to the action of the mammalian eye. In a very useful embodiment, the force transfer assembly is adapted to transfer force from the eye to the optic to facilitate reshaping of the optic or reshaping of the optic and moving the optic axially in the eye. The force transfer assembly is very effective in facilitating the accommodation obtained by the present IOLs.

However, it should be noted that such force transfer assembly is not essential in accordance with the present invention. The optic can be sized and configured to fit within the capsular bag and to contact the capsular bag, in particular the periphery of the capsular bag, so that the force exerted by the eye can be transferred directly to the optic of the present IOL. Such IOLs in which the optics are sized and configured to contact the peripheral capsular bag are very effective in being reshaped to provide the desired accommodation. In addition, substantially filling the capsular bag volume with a deformable optic including a first lens portion and a second lens portion, as in the present optics, reduces the risk of decentration or tilt of the lens system in the eye, as well as reducing the risk of decentration or tilt between individual lens components, relative to lens systems in which the optic does not substantially fill the capsular bag volume. Providing for a reduced risk of decentration is highly advantageous, for example, as the capsular bag contracts. Even if the contraction of the capsular bag is asymmetric, for example, because the zonules are not of uniform strength, the elastic properties of the first portion mitigate against this asymmetry and reduce the risk of decentration.

Substantially filling the capsular bag volume, as described above, may reduce the risk of posterior capsular opacification (PCO) particularly if the posterior surface of the optic remains in contact with the posterior wall of the capsular bag during all states of accommodation.

In a very useful embodiment, the present IOLs are deformable for insertion into the mammalian eye through a relatively small incision, for example on the order of about 3.5 mm or less. Thus, both the first and second lens portions of the optic, and the force transfer assembly, if present, are all deformable for insertion through a small incision into the eye. Such IOLs regain their original undeformed condition rapidly after being inserted into the mammalian eye.

In order to facilitate the movement in the eye, the first portion preferably is more deformable than the second portion of the present IOLs. As noted previously, the second portion can be substantially rigid, for example, in response to forces exerted in the eye. However, it is preferred that the entire IOL be sufficiently deformable to be passed through an incision in the eye which is less than the diameter of the IOL in its undeformed condition.

The present optics may be made of any suitable materials of construction. For example, the present optics may be made of one or more polymeric materials employing techniques used in manufacturing conventional polymeric material IOLs. Examples of the materials from which the present optics can be made include, without limitation, acrylic polymeric materials, silicone polymeric materials, and the like and combinations thereof. Although combinations of different polymeric materials may be employed, the present optics preferably are made of different polymeric materials of the same general chemical family. For example, the first lens portion of the IOL may be made of one silicone polymeric material while the second portion is made of a different silicone polymeric material. Similarly, the first portion of the optic can be made of one acrylic polymeric material while the second lens portion is made of a different acrylic polymeric material. In any event, the first portion of the present optics and the second portion and third portion, if present, preferably are made of compatible materials of construction, that is materials which can be used to produce an effective IOL which remains as an intact structure in the eye without significant deterioration for periods of time extending for at least about 20 or about 25 years or more.

In one embodiment, the first lens portion of the present optics is made of a very low modulus silicone polymeric material, while the second portion is made of a higher refractive index silicone. To illustrate, the first portion of the optic can be composed of a silicone polymeric elastomer with the following material properties:

Optically clear;
Refractive index of at least about 1.37;
Shore A hardness of about 0; and
At least about 1000% elastic elongation.

The second lens portion of the present optics can be made of a different silicone elastomer with the following material properties:

Optically clear;
Refractive index of about 1.42 or higher;
Shore A hardness in a range of about 0 to about 30; and
An elastic elongation higher than about 150%, preferably in a range of about 150% to about 400%.

The second lens portion can be made of widely varying materials. Examples include, without limitation, rigid and foldable acrylic polymeric materials, rigid and foldable non-acrylic polymeric materials, deformable or foldable silicone polymeric materials and the like and combinations thereof. The second portion can be hydrophobic or hydrophilic.

Many materials which meet the above-noted criteria are conventional and well known in the art. Therefore, a detailed description of such compositions is not presented here.

However, by way of illustration, the following materials of construction, based on constituent monomeric components, is presented.

TABLE

POTENTIAL FORMULATIONS

| Component | First Portion | Second Portion |
|---|---|---|
| 2-phenylpropyl acrylate } 2-phenylpropyl methacrylate | 50% wt. | 70% wt. |
| Ethylene glycol dimethacrylate | 0.5% wt. | 1.0% wt. |
| N-hexyl acrylate | 48.9% wt. | 28.4% wt. |
| UV chromophore (benzotriazole-type) | 0.5% wt. | 0.5% wt. |
| Initiator | 0.1% wt. | 0.1% wt. |

The present optics are conveniently produced using conventional and well known techniques, such as molding techniques. In one embodiment, the second portion is produced in a separate mold and then inserted into a mold into which is placed the monomeric or partially polymerized monomeric mixture of the first portion precursors. The combination is then heated to elevated temperatures, for example on the order of about 40° C. to about 100° C., and/or subjected to ultraviolet radiation and the composition combination is allowed to cure, preferably for about one hour to about 24 hours. The material in the mold is then post-cured, preferably at a temperature in the range of about 70° C. to about 130° C., and/or being subjected to ultraviolet radiation for a period of time, preferably for about two hours to about 30 hours. After curing (and post-curing), the mold is disassembled and the molded lens body recovered.

The force transfer assembly, if present, can be made or provided separately and then coupled to the optic or lens body, for example, in a mold in which the optic is cured or post-cured. Alternately, the force transfer assembly can be coupled to the lens body after the lens body is formed. Conventional techniques can be employed. For example, one or more recesses can be formed in the optic and the force transfer assembly can be secured to the optic by having an end placed in the recess, for example, in much the same manner in which a haptic or fixation member is secured to the optic of a conventional IOL.

Any suitable material or combination of materials of construction may be utilized in the force transfer assembly and the force transfer assembly can have any suitable configuration provided that such assembly is effective to at least partially transfer the force of the eye to the optic of the IOL. The force transfer assembly preferably is more rigid or less flexible than the first portion of the optic. However, the force transfer assembly preferably is sufficiently deformable to be folded or otherwise deformed to pass through a small incision for insertion into the eye. The force transfer assembly can be a single member substantially surrounding the optic, or can be a plurality, for example, about 2 or about 3 to about 4 or about 6, individual elements positioned around the peripheral edge of the optic. Although the force transfer assembly can include at least one hinge to facilitate axial movement of the optic in response to the action of the eye, preferably the force transfer assembly does not include a hinge.

The force transfer assembly preferably is made of a material or materials which are compatible with the eye and with the other material or materials included in the IOL. Examples of materials which can be included in the present force transfer assemblies include, but are not limited to, polypropylene, silicone polymeric materials, acrylic polymeric materials including but not limited to polymethylmethacrylate (PMMA), polyamides and the like and combinations thereof.

In a further broad aspect of the present invention, methods for inserting an IOL in an eye are provided. Such methods comprise providing an IOL in accordance with the present invention, as described herein. The IOL is placed into the eye, for example in the capsular bag of the eye, using equipment and techniques which are conventional and well known in the art. The IOL is placed in the eye so that the eye effectively cooperates with the IOL to provide accommodation as desired. After the IOL is inserted into the eye, any incision in the eye is closed. After a relatively short period of recuperation, the IOL provides the wearer of the IOL with substantially effective accommodation. No further treatments or medications, for example, to paralyze the ciliary muscle, to facilitate fibrosis or otherwise influence the position of the IOL in the eye, are required. Preferably the optic is deformed prior to being placed into the eye. Once the IOL is placed in the eye, and after a normal period of recovery from the surgical procedure, the IOL, in cooperation with the eye, provides the mammal or human wearing the IOL with the desired accommodation.

Any and all features described herein and combinations of such features are included within the scope of the present invention provided that the features of any such combinations are not mutually inconsistent.

Additional aspects and advantages of the present invention are set forth in the following description and claims, particularly when considered in conjunction with the accompanying drawings in which like parts bear like reference numerals.

BRIEF DESCRIPTION OF THE DRAWINGS

FIG. 4 is a top side view, in perspective, of an additional IOL in accordance with the present invention;

FIG. 5 is a fragmentary sectional view of an eye in which the IOL of FIG. 4 has been implanted with the lens being located in a resting position with the ciliary muscle of the eye in the relaxed state;

FIG. 6 is a fragmentary sectional view of an eye in which the IOL of FIG. 4 has been implanted, with the ciliary muscle of the eye in the contracted state.

DETAILED DESCRIPTION OF THE DRAWINGS

Figure 1:
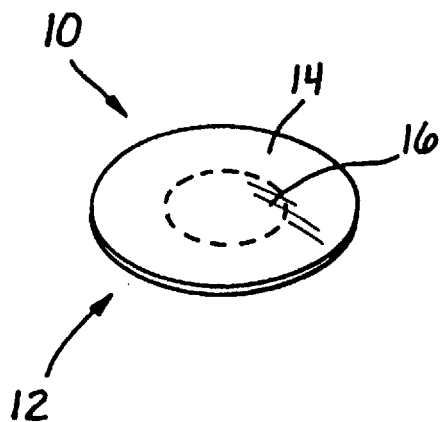
FIG. 1 is a top side view, in perspective, of an IOL in accordance with the present invention.
Figure 2:
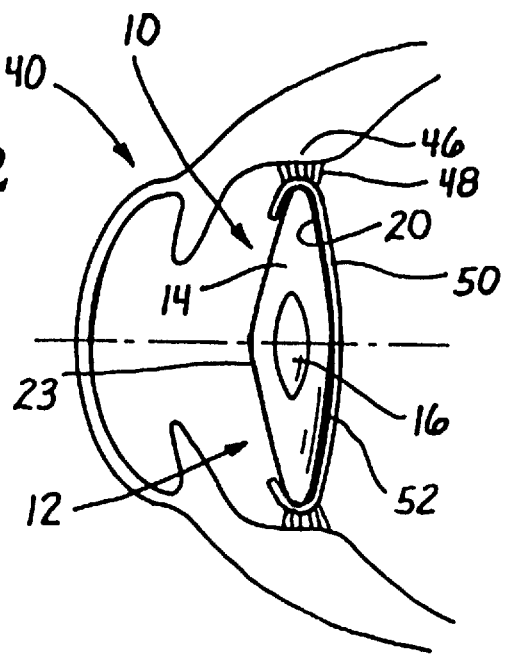
FIG. 2 is a fragmentary sectional view of an eye in which the IOL of FIG. 1 has been implanted, with the lens being located in a resting position with the ciliary muscle of the eye in the relaxed state.
Figure 3:
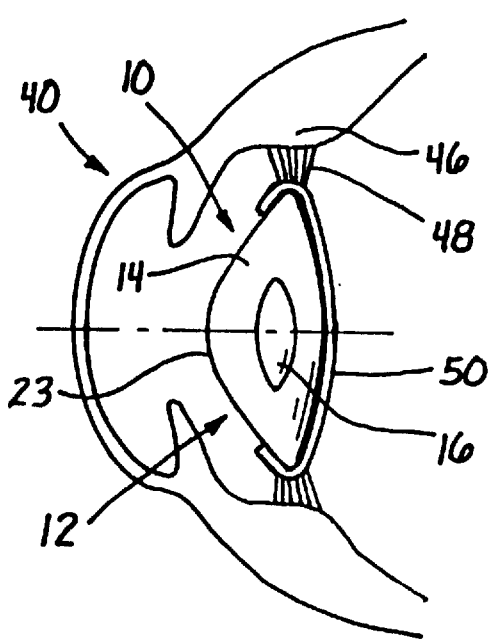
FIG. 3 is a fragmentary sectional view of an eye in which the IOL of FIG. 1 has been implanted, with the ciliary muscle of the eye in the contracted state.

Referring now to FIGS. 1, 2 and 3, an IOL according to the present invention, shown generally at 10, includes a lens body or optic 12. This optic 12 includes a combination of components, that is, outer portion 14 and inner or surrounded portion 16. Outer portion 14 completely surrounds inner portion 16 which is secured to the outer portion.

The inner lens portion 16 is made of an optically clear material with a refractive index of at least about 1.42, for example, about 1.48. Further, the inner lens portion 16 can be either deformable or rigid. Preferably the inner lens portion 16 is sufficiently deformable so as to be foldable or otherwise deformable for insertion into the eye through a small incision, that is an incision in the eye smaller than the maximum, undeformed diameter of the optic 12. However, the inner lens portion 16 preferably is more rigid than is the outer lens portion 14.

The outer lens portion 14 is comprised of an optically clear material that is easily deformable when subjected to the action, that is the contraction or contractive force, exerted by the ciliary muscle of the eye. As noted above, the inner lens portion 16 has a higher refractive index relative to the refractive index of the outer lens portion 14 of optic 12.

The outer lens portion 14 and the inner lens portion 16 preferably is comprised of materials from the same basic chemical family. For example, the outer lens portion 14 may be comprised of low or very low modulus silicone polymeric material having an index of refraction of at least about 1.37 or about 1.39, while the inner lens portion 16 can be comprised of higher refractive index silicone, for example having an index of refraction of at least about 1.42 or at least about 1.44 or about 1.46 or about 1.48 or higher. The modulus of the silicone polymeric material making up the outer lens portion 14 is, for example, no greater than about 20 psi.

Alternately, the outer lens portion 14 can be comprised of a hydrophilic acrylic polymeric material, while the inner lens portion 16 can be made of higher refractive index, rigid or deformable (for insertion) acrylic polymeric materials which can be either hydrophobic or hydrophilic.

One example of the materials used to produce the outer lens portion 14 and the inner lens portion 16 are as follows:

TABLE

POTENTIAL FORMULATIONS

| Component | Outer Portion | Inner Portion |
|---|---|---|
| 2-phenylpropyl acrylate<br>2-phenylpropyl methacrylate | 50% wt. | 70% wt. |
| Ethylene glycol dimethacrylate | 0.5% wt. | 1.0% wt. |
| N-hexyl acrylate | 48.9% wt. | 28.4% wt. |
| UV chromophore (benzotriazole-type) | 0.5% wt. | 0.5% wt. |
| Initiator | 0.1% wt. | 0.1% wt. |

The present IOL 10 can be produced using conventional polymer processing techniques. For example, the present inner lens portions 16 can be produced separately using conventional molding, for example, injection molding, techniques. This inner lens portion 16 can then be used to produce optic 12 using conventional molding techniques, for example, insert molding techniques, together with the material used to produce the outer lens portion 14.

The optical powers of the lens portions 14 and 16 may be controlled so as to satisfactorily address the needs of the patient in whose eye IOL 10 is inserted. Each of the lens portions 14 and 16 can have a suitable optical power.

The optical power of the optic 12 is a combination of the optical powers of the individual lens portions 14 and 16, and can be varied based on the individual optical powers of the portions 14 and 16 and the degree of reshaping and/or axial movement of the optic 12.

The IOL 10 is sized to fit within the capsular bag 50 of the eye 40 so as to be reshapable in response to the action of the ciliary muscle 46 and zonules 48 on the capsular bag of the eye. The IOL 10 should be sized to facilitate the movement and reshaping of the optic 12 in response to the action of the ciliary muscle 46 and zonules 48. For example, if the optic 12 is too large, the ciliary muscle 46 and zonules 48 will be inhibited from effectively contracting/relaxing so that the amount of accommodating movement and reshaping will be unduly restricted. Of course, if the IOL 10 is too small, the optic 12 will be ineffective to focus light on the retina of the eye 40, may cause glare and/or may not cooperate with the eye to effect the desired amount of accommodating movement/reshaping. If the IOL 10 is to be included in an adult human eye, the optic 10 preferably has a diameter in the range of about 8 mm to amount 12 mm.

The IOL 10 can be inserted into the capsular bag 50 of the eye 40 using conventional equipment and techniques, for example, after the natural crystalline lens of the eye is removed, using a phacoemulsification technique.

The IOL 10 in the eye 40, as shown in FIGS. 2 and 3, is located so that the posterior face 20 of the outer lens portion 14 is in contact with the inner posterior wall 52 of the capsular bag 50. This contact is substantially maintained regardless of the configuration of the optic 12 in the eye 40. Such contact is effective in maintaining the structural integrity of the capsular bag 50 and, in addition, effectively inhibits the growth of cells from the capsular bag onto the optic, thereby at least inhibiting or reducing the severity of posterior capsular bag opacification (PCO).

Without wishing to limit the invention to any particular theory or mode of operation, the eye 40 is believed to act on optic 12 as follows. With the ciliary muscle 46 fully relaxed, the tension of the zonules 48 causes the capsular bag 50 to increase in diameter which causes the optic 12 to be in a relatively flat or thin configuration. Such configuration of optic 12 provides effective distance vision to the eye 40. This configuration is at least generally illustrated in FIG. 2. With IOL 10 in the position as shown in FIG. 2, far away or distant objects are brought into focus. If a near object is to be viewed, the ciliary muscle 46 contracts or constricts. The capsular bag 50 compresses, reshaping the optic 12 to a relatively thick configuration and increasing the curvature of the anterior face 23 of the outer lens portion 14. The outer lens portion 14 is relatively more reshaped than the inner lens portion 16, which may remain substantially in its original shape in response to the action of the eye. This relatively thick configuration of optic 12, in particular the increased curvature of the anterior face 23, generally illustrated in FIG. 3, provides near focus accommodation to allow the near object to be viewed.

The present IOL 10 has the ability, in cooperation with the eye, to be reshaped to provide for both distance focus and near focus.

One important advantage of the present IOL 10 is the controlled reshaping of optic 12 and in particular of outer lens portion 14. Such reshaping provides effective accommodation. The inner lens portion 16 increases or enhances the stability of the optic 12 in the eye and facilitates the effective, controlled reshaping of the outer lens portion 14. In addition, the inner lens portion 16 advantageously has an optical power which, together with the outer lens portion 14, satisfies the distance vision requirements of the wearer of IOL 10 with the optic 12 in the relatively flat or thin configuration (FIG. 2).

IOL 10 is such that the amount of accommodation achievable preferably is in the range of about 1 to about 4 or about 5 or about 6 diopters.

FIGS. 4, 5 and 6 illustrate an additional IOL, shown generally at 110, in accordance with the present invention. Except as expressly described herein, additional IOL 110 is structured and functions similarly to IOL 10. Components of IOL 110 which correspond to components of IOL 10 are indicated by the same reference numerals increased by 100.

The primary difference between IOL 110 and IOL 10 relates to the presence in IOL 110 of a force transfer assembly, shown generally at 70. In particular, as best shown in FIG. 4, force transfer assembly 70 includes four identically structured transfer members 72 which extend radially outwardly from the proximal end 74, which is attached to optic 112, to an outer or distal end 76. Each of the transfer members 72 has a substantially flat configuration and is made of an acrylic polymeric material which is deformable for insertion of the IOL 110 into the eye, yet is more rigid than the outer lens portion 114 to facilitate the transfer of force from the eye 140 to the optic 112. One particularly useful acrylic polymeric material for use as a material of construction of the members 72 is a polymeric composition produced from the following mixture of monomers:

| | |
|---|---|
| Ethyl acrylate | 57.1% by weight |
| Ethyl methacrylate | 27.7% by weight |
| Trifluoroethyl methacrylate | 9.8% by weight |
| Ethylene glycol dimethacrylate | 3.8% by weight |
| UV chromophore | 1.5% by weight |
| Initiator (thermal) | 0.1% by weight |

The IOL 110 can be produced by injection molding the inner lens portion 116, and transfer members 72 separately and then insert molding can be employed to form the combination of the inner lens portions, the transfer members and the outer lens portion 114.

With the force transfer assembly 70 in place, if the IOL 110 is to be included in an adult human eye, the optic 112 preferably has a diameter in the range of about 3.5 mm to about 7 mm, and the IOL 110 has an overall maximum diameter, including the force transfer assembly 70 in the rest state, that is fully extended from the optic 112, in the range of about 8 mm to about 12 mm.

Insertion can be accomplished using conventional techniques, for example, after the natural lens of the eye has been removed.

In the eye, IOL 110 moves axially in response to the action of the eye 140, which includes ciliary muscle 146 and zonules 148, through the force transfer assembly 70. In addition, the optic 112 is reshaped in response to the action through force transfer assembly 70. The posterior face 120 of outer lens portion 114 remains in substantial contact with the inner posterior wall 152 of the capsular bag 150. Such contact occurs whether the IOL 110 is located in its posterior most position in eye 140 or in its anterior most position in eye 140. Such contact inhibits the growth of cells from the capsular bag 150 onto optic 110 and inhibits PCO.

IOL 110 provides focus accommodation because of the reshaping of the optic 112, in much the same way as when optic 12 is reshaped. However, optic 112 provides further accommodation because of the axial movement of optic 112. Thus, optic 112 may provide additional or enhanced accommodation relative to optic 12.

The present invention provides accommodating IOLs which cooperate with the eye to achieve advantageous amounts, preferably enhanced amounts, of accommodation. Such accommodation, as described herein, is often increased, for example relative to previous accommodating IOLs.

While this invention has been described with respect to various specific examples and embodiments, it is to be understood that the invention is not limited thereto and that it can be variously practiced within the scope of the following claims.

What is claimed is:

1. An intraocular lens for use in a mammalian eye, comprising:
   an optic structured to focus light toward a retina of the mammalian eye and, in cooperation with the mammalian eye, to provide accommodation, the optic including:
   a first lens portion structured to be reshaped in response to the action of the mammalian eye;
   a second lens portion surrounded by and embedded centrally in the first lens portion and having a higher index of refraction than the first lens portion; and
   a force transfer assembly coupled to the optic and structured to contact a surrounding posterior bag of the mammalian eye when the intraocular lens is located in the mammalian eye, the force transfer assembly being more rigid than the first lens portion and structured to transmit a force exerted by the eye to the optic to facilitate movement of the optic.

2. The intraocular lens of claim 1, wherein the force transfer assembly includes separate transfer members each having a first end coupled to the optic and a second end extending away from the optic and structured to contact the surrounding posterior bag of the mammalian eye.

3. The intraocular lens of claim 2, wherein there are four identically structured transfer members.

4. The intraocular lens of claim 2, wherein each of the transfer members has a substantially flat configuration.

5. The intraocular lens of claim 1, wherein the force transfer assembly is made of an acrylic polymeric material.

6. The intraocular lens of claim 5, wherein the acrylic polymeric material is a composition of monomers predominantly including ethyl acrylate and ethyl methacrylate.

7. The intraocular lens of claim 1, wherein the index of refraction of the second lens portion is at least about 1.42.

8. The intraocular lens of claim 1, wherein the first lens portion includes an anterior surface and is adapted to be reshaped in response to the action of the mammalian eye, the reshaping being effective to change the curvature of the anterior surface.

9. The intraocular lens of claim 1, wherein the first lens portion is structured to move axially in the mammalian eye in response to the action of the mammalian eye.

10. The intraocular lens of claim 9, wherein the first lens portion includes an anterior surface and is adapted to be reshaped in response to the action of the mammalian eye, the reshaping being effective to change the curvature of the anterior surface.

11. The intraocular lens of claim 1, wherein the optic is deformable for insertion into the mammalian eye through a small incision.

12. The intraocular lens of claim 1, wherein the first lens portion is more deformable than the second lens.

13. The intraocular lens of claim 1, wherein the optic comprises materials selected from the group consisting of acrylic polymeric materials and silicone polymeric materials.

14. The intraocular lens of claim 13, wherein the first lens portion comprises a material selected from the group consisting of hydrophilic acrylic polymeric materials and low modulus silicone polymeric materials.

15. The intraocular lens of claim 13, wherein the second lens portion comprises a material selected from the group consisting of hydrophobic polymeric materials and hydrophilic polymeric materials.

16. The interocular lens of claim 13, wherein the first lens portion and the second lens portion are made of different polymeric materials of the same general chemical family.

17. The intraocular lens of claim 1, wherein the intraocular lens is produced by a process including injection molding the second lens portion and force transfer assembly separately, and then using insert molding to form the combination of the first lens portion, second lens portion and force transfer assembly.

18. The intraocular lens of claim 17, wherein the force transfer assembly includes separate transfer members each having a first end coupled to the optic and a second end extending away from the optic.

19. An intraocular lens for use in a mammalian eye, comprising:
 an optic structured to focus light toward a retina of the mammalian eye and, in cooperation with the mammalian eye, to provide accommodation, the optic including:
  a first lens portion is made of a hydrophobic polymer and structured to be reshaped in response to the action of the mammalian eye; and
  a second lens portion surrounded by and embedded centrally in the first lens portion and having a higher index of refraction than the first lens portion.

20. The intraocular lens of claim 19, wherein the second lens portion is substantially rigid in response to forces exerted by the eye.

21. The intraocular lens of claim 19, wherein the first lens portion includes an anterior surface and is adapted to be reshaped in response to the action of the mammalian eye, the reshaping being effective to change the curvature of the anterior surface.

22. The intraocular lens of claim 19, wherein the optic is deformable for insertion into the mammalian eye through a small incision.

23. The intraocular lens of claim 19, wherein the first lens portion is more deformable than the second lens portion.

24. The intraocular lens of claim 19, wherein the optic comprises materials selected from the group consisting of acrylic polymeric materials and silicone polymeric materials.

25. The interocular lens of claim 24, wherein the first lens portion and the second lens portion are made of different polymeric materials of the same general chemical family.

26. The intraocular lens of claim 25, wherein the first lens portion and the second lens portion are made of an acrylic polymeric material having a composition that is at least 50% 2-phenylpropyl acrylate, 2-phenylpropyl methacrylate.

27. The intraocular lens of claim 25, wherein the second lens portion is a hydrophobic acrylic polymeric material.

28. The intraocular lens of claim 19, further including a force transfer assembly coupled to the optic and structured to contact a surrounding posterior bag of the mammalian eye when the interocular lens is located in the mammalian eye, the force transfer assembly being structured to transfer the force exerted by the eye the optic to facilitate movement of the optic.

29. The intraocular lens of claim 28, wherein the force transfer assembly includes separate transfer members each having a first end coupled to the optic and a second end extending away from the optic and structured to contact a surrounding posterior bag of the mammalian eye.

30. The intraocular lens of claim 29, wherein there are four identically structured transfer members.

31. The intraocular lens of claim 29, wherein each of the transfer members has a substantially flat configuration.

32. The intraocular lens of claim 28, wherein the force transfer assembly is made of an acrylic polymeric material.

33. The intraocular lens of claim 28, wherein the force transfer assembly is coupled to the first lens portion and made of a material that is more rigid than the first lens portion.

34. The intraocular lens of claim 28, wherein the force transfer assembly is structured to transfer the force exerted by the eye to the optic to facilitate axial movement of the second lens portion.

35. The intraocular lens of claim 34, wherein the first lens portion includes an anterior surface and is adapted to be reshaped in response to the action of the mammalian eye, the reshaping being effective to change the curvature of the anterior surface.

36. The intraocular lens of claim 19, wherein the index of refraction of the second lens portion is at least about 1.42.

37. The intraocular lens of claim 36, wherein the index of refraction of the first lens portion is at least about 1.37.

* * * * *